United States Patent [19]

Hobish et al.

[11] Patent Number: 5,044,950
[45] Date of Patent: Sep. 3, 1991

[54] THERAPEUTIC TRAINING DEVICE AND METHOD FOR FITTING DENTURES

[76] Inventors: Stanley Hobish, 4 Oxford Pl., Massapequa; Sheldon M. Weiss, 48 Captains Dr., Islip, both of N.Y. 11758

[21] Appl. No.: 444,001

[22] Filed: Nov. 29, 1989

[51] Int. Cl.⁵ .............................. A61C 19/04
[52] U.S. Cl. ........................... 433/69; 433/68
[58] Field of Search ................ 433/6, 68, 69, 71, 197

[56] References Cited

U.S. PATENT DOCUMENTS

| | | | |
|---|---|---|---|
| 2,027,373 | 1/1936 | Eden | 433/69 |
| 2,389,063 | 11/1945 | Lang | 433/69 |
| 2,617,192 | 11/1952 | Goddard | 433/197 |
| 3,068,570 | 12/1962 | Thompson | 433/69 |
| 3,252,220 | 5/1966 | Goddard | 433/197 |
| 4,332,556 | 6/1982 | Daiberl | 433/69 |
| 4,671,766 | 6/1987 | Norton | 433/6 |
| 4,810,192 | 3/1989 | Williams | 433/6 |

OTHER PUBLICATIONS

"Office Procedure for Extended Swiss Denture Service", Swissedent Corporation, Jun. 1969.
"The Original Ball Bearing Bite Recorder Technique Manual and Catalog", Comfort Hold Dental Systems.
"The Comfort Hold Denture System" Comfort Hold Dental Systems.
Videotape narrated by Dr. Stanley Hobish which was shown more than one year prior to the filing of the above-identified application.

Primary Examiner—John J. Wilson
Assistant Examiner—Cindy A. Cherichetti
Attorney, Agent, or Firm—Ostrolenk, Faber, Gerb & Soffen

[57] ABSTRACT

A training device for therapeutically exercising a protruding mandible of an edentulous individual to reposition the same to an optimal position. The training device is part of a total system for fitting an edentulous individual with dentures that includes first repositioning the mandible to its optimal position using the training device, and then maintaining the repositioned mandible in place using dentures having a concave masticating surface and a ridge along one edge of the masticating surface.

6 Claims, 3 Drawing Sheets

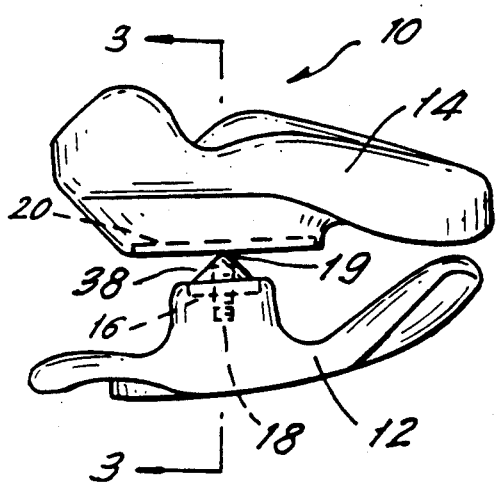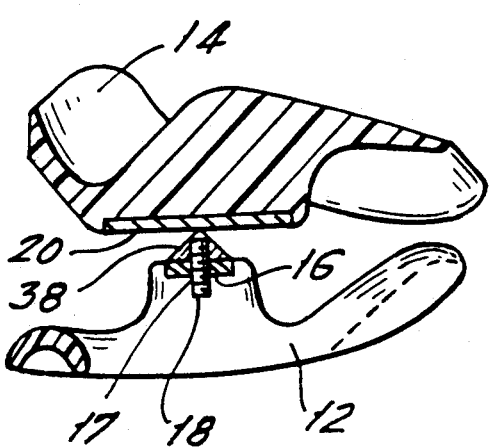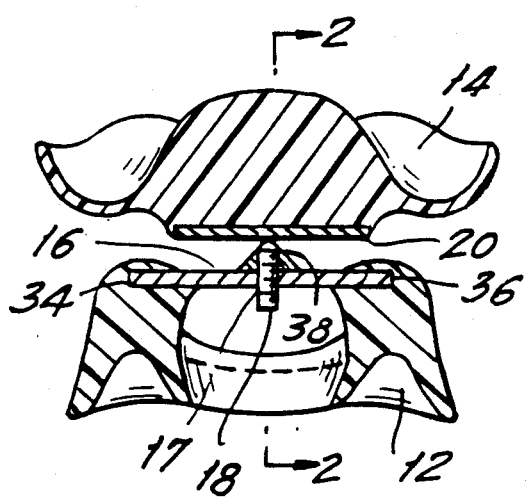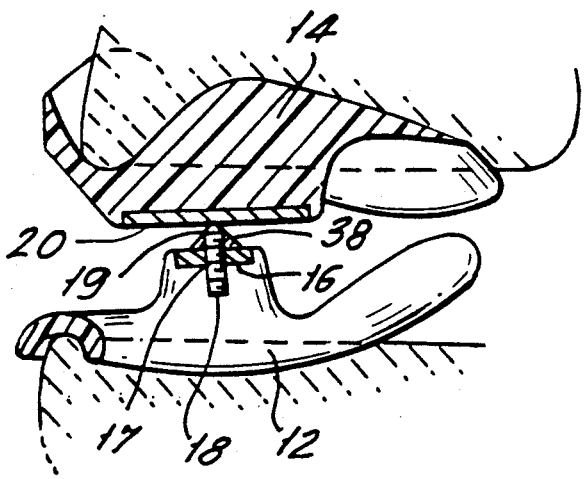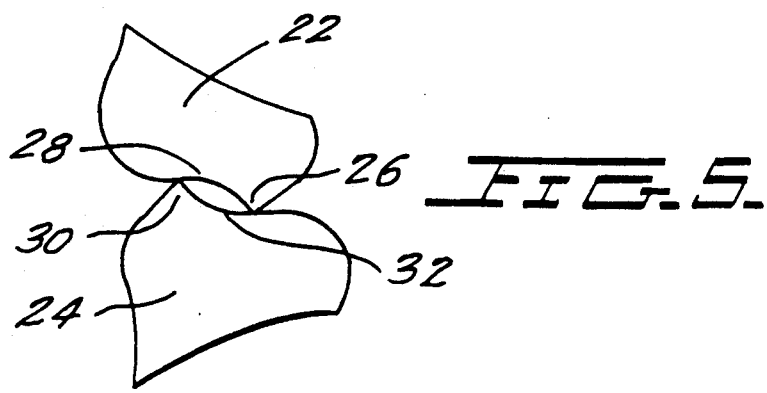

FIG. 6.
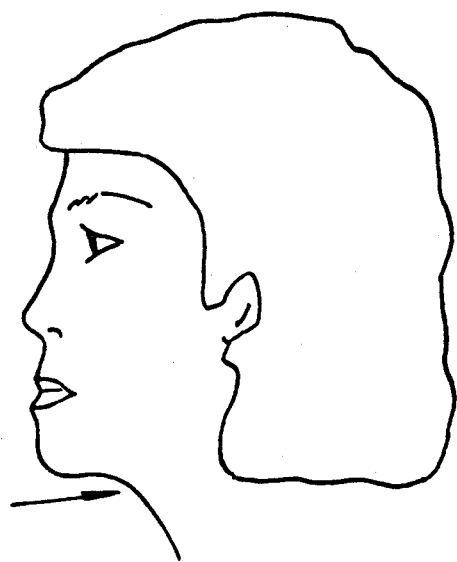
FIG. 7.
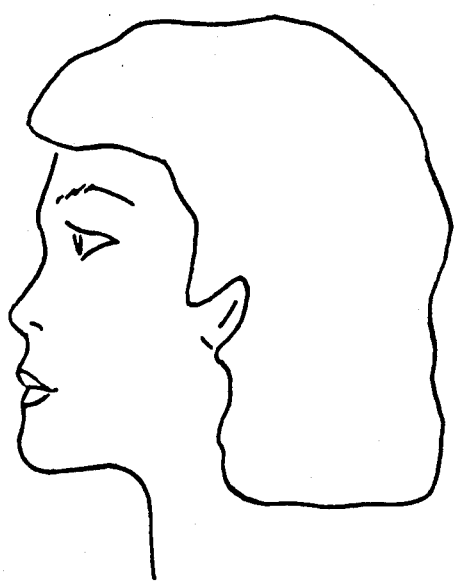
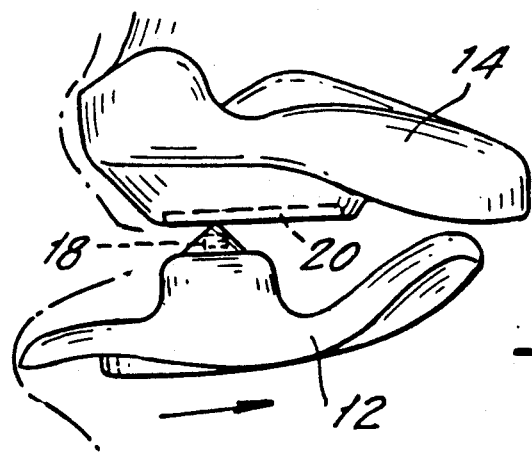
FIG. 8.
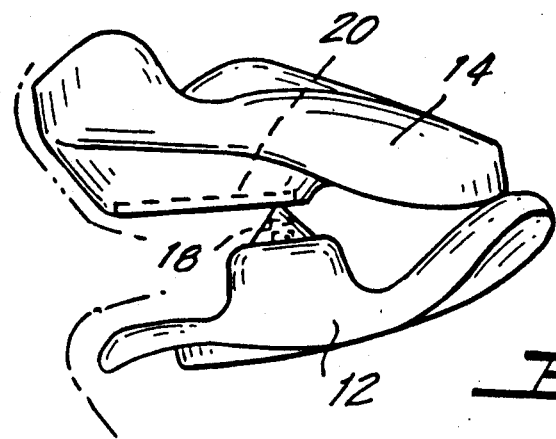
FIG. 9.

THERAPEUTIC TRAINING DEVICE AND METHOD FOR FITTING DENTURES

BACKGROUND OF THE INVENTION

1. Field of the Invention

The present invention relates to a therapeutic training device for posteriorly repositioning the lower jaw of an edentulous or toothless patient to its optimal position. The invention also relates to a system for fitting an edentulous patient with dentures using such a device.

2. Description of the Related Prior Art

Individuals who wear dentures for an extended period of time experience a drifting forward of their mandible as can be seen by the protruded position of the mandible in the facial profile illustrated in FIG. 6 as compared to the profile shown in FIG. 7. This condition impairs the function of artificial teeth since such teeth are manufactured for a particular patient's bite at the time before the mandible has drifted forward. The drifting forward of the mandible also detracts from the individual's appearance.

Devices are known which can be used to treat conditions of the temporomandibular joint (TMJ), i.e., the joint between the temporal bone or the compound bone on the side of the skull of humans and the mandible.

U.S. Pat. No. 4,671,766 to Norton discloses an intraoral, orthotic device for stabilizing the muscles used for mastication. The device includes two halves, one for the maxillary arch and one for the mandibular arch. Both halves have projecting wings that interact when the mouth is closed to exercise the jaw muscles.

U.S. Pat. No. 4,810,192 to Williams discloses a device used for healing the TMJ after it has been subjected to trauma. A first stage of the device acts as a mandibular orthodontic repositioning appliance, and a second stage is a mouth guard providing maxillary and mandibular teeth seats. The two stages interact together when positioned in the mouth to protect the upper and lower teeth and hold the TMJ in its functional position.

It is also known in the art to employ bite plates fitted into the mouth of a patient to record the patient's bite. The patient makes an uninterrupted, oscillatory motion of a lower bite plate relative to an upper bite plate, and in doing so traces a so-called "Gothic Arch" on a contact plate mounted onto one of the bite plates. Similar devices are used to correlate or equilibrate dentures in the mouth of the patient so that they will be balanced for proper contact and comfort to the wearer.

U.S. Pat. No. 3,068,570 to Thompson et al., for example, discloses a dental device including a lower and upper dental plate. Mounted to the lower dental plate is a base member having a striking pin attached thereto. Mounted on the upper dental plate is a contacting plate. The striking pin is used to trace a Gothic Arch on the contact plate.

Thompson et al. teaches that its invention is particularly useful when used in conjunction with certain artificial teeth disclosed in U.S. Pat. No. 2,617,192 to Goddard. Another patent relating to these types of artificial teeth is U.S. Pat. No. 3,252,220 also to Goddard. The Goddard '220 patent teaches dentures including teeth having a masticating surface which is concave and which includes a ridge on one edge which contacts the masticating surface of a corresponding tooth. For reasons which will become clear later, this type of artificial teeth is preferred for use in connection with the present invention.

The device disclosed in Thompson et al. has never before been used to treat the TMJ. The invention utilizes such a device (modified with certain additional features which will be discussed below) as a training device in combination with artificial teeth of the type disclosed in Goddard '220 to reposition the mandible posteriorly and maintain the repositioned mandible in its optimal position for its function and aesthetics. The training device is used by a patient over a period of several weeks to exercise the muscles of the face and jaws and urge the mandible to go back to its original, optimal position. After this has occurred, the optimal centric position is captured in plaster and casts mounted, as is conventional, to fit an individual with dentures. The dentures utilize teeth of the type disclosed in Goddard '220 and become, in effect, a therapeutic device that continues to accommodate any further posterior repositioning the mandible may make.

When the dentures are made in this way, i.e., when an edentulous individual's mandible is correctly positioned prior to being fitted with dentures, a patient experiences significantly less movement of the denture bases on the gum tissue and hence much less soreness and discomfort.

SUMMARY OF THE INVENTION

Accordingly, it is an object of the present invention to provide a device and method for repositioning the mandible of an edentulous individual to the position it occupied prior to the loss of teeth.

Another object of the invention is to retrain the muscles of mastication to function properly with the mandible relating to the maxilla at the normal vertical dimension.

A further object of the invention is to relieve the stress on the muscles, ligaments and other anatomic structures of the TMJ.

A still further object of the invention to provide a total system and method for fitting such an individual with artificial teeth such that the artificial teeth function optimally and with minimum amount of discomfort to the user.

These and other objectives are achieved by providing a therapeutic, intraoral training device that repositions the mandible of an edentulous individual whose mandible has drifted forward to a protruding position. The device comprises a lower and upper denture plate adapted to fit over the lower and upper gums of the individual, respectively. The lower denture plate includes a base member comprising a substantially flat and rectangular plate that is mounted onto an upper portion of the lower denture plate, and a striking pin that is received within the base member and is positioned at about 90° with respect to the base member. The upper denture plate includes a contact plate mounted onto its lower portion. The striking pin contacts the contact plate when the individual closes his mouth, urging the mandible of the individual to be repositioned posteriorly. Movement of the mandible is indicated by indicating means having a grid so that full repositioning for optimal function of the mandible and aesthetics can be determined by visual inspection of the grid.

A method is also provided for repositioning the mandible which includes using the intraoral, training device described above for an amount of time until the mandible has been repositioned posteriorly.

A total system is provided for fitting an edentulous individual with dentures. The system comprises the combination of the therapeutic, intraoral training device described above for repositioning the mandible and dentures with teeth constructed for maintaining the repositioned mandible in place.

A method for fitting the edentulous individual with dentures is also provided whereby the individual uses the therapeutic, intraoral training device described above until the mandible has been optimally repositioned, and then uses the dentures described above to maintain the repositioned mandible in its optimal position.

BRIEF DESCRIPTION OF THE DRAWINGS

Other features and advantages of the present invention will become apparent when the following description is read in conjunction with the accompanying drawings, in which:

FIG. 1 shows a side view of the training device of the invention.

FIG. 2 shows a side, cross-sectional view of the training device along lines 2—2 shown in FIG. 3.

FIG. 3 shows a cross-sectional view of the training device viewed from the back of the device along lines 3—3 shown in FIG. 1.

FIG. 4 shows a cross-sectional view of the training device positioned in an edentulous individual's mouth on the lower and upper gums (shown only partially), and the angled orientation of a contact plate and striking pin of the device at such a position.

FIG. 5 shows the profile of two cooperating artificial teeth of a set of dentures that are used in conjunction with the training device to maintain the repositioned mandible in its correct position.

FIG. 6 shows an edentulous individual whose mandible has drifted forward into a protruded position.

FIG. 7 shows the same individual after using the training device and after the protruding mandible shown in FIG. 6 has been repositioned.

FIG. 8 shows the relative positions of components of the training device in position in an individual's mouth (shown only partially in phantom lines) at the time when the individual begins use of the training device in accordance with the invention.

FIG. 9 shows the relative positions of the same components of the training device after the individual has completed use of the training device and the protruding mandible shown in FIG. 6 has been repositioned posteriorly in accordance with the invention.

DETAILED DESCRIPTION OF THE PREFERRED EMBODIMENT

Figure 5A:
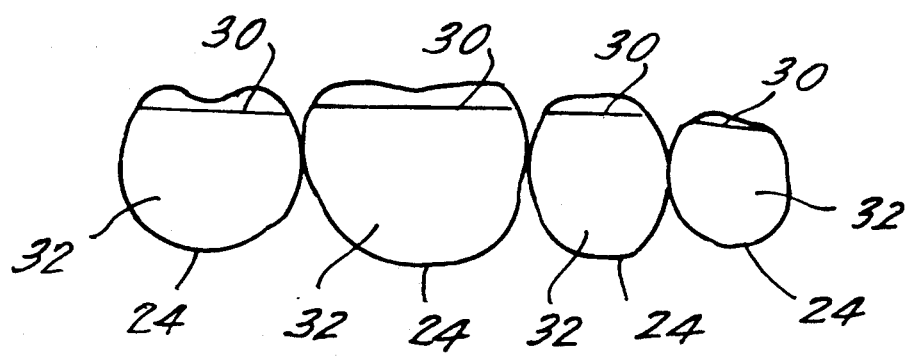
FIG. 5a shows a top plan view of a portion of a total denture set showing the masticating surface and ridges of several adjacent posterior artificial teeth.

Referring first to FIGS. 1-4, the training device of the invention, identified generally by reference numeral 10, includes a lower denture plate 12 and an upper denture plate 14. Lower plate 12 and upper plate 14 are known as a "denture base" and are shaped such that they fit into an edentulous individual's mouth and over the lower and upper gums of the individual, respectively. Such plates are usually made of a thermoplastic material. As mentioned, except for certain modifying features which will be discussed below, training device 10 generally corresponds to the device disclosed in U.S. Pat. No. 3,068,570, which is herein incorporated by reference.

A base member 16 is mounted upon lower denture plate 12. Base member 16 is a substantially flat and rectangular plate arranged generally transverse to the lower denture plate 12. As can be seen in FIG. 3, two opposite ends 34 and 36 of base member 16 are embedded within lower denture plate 12 while the central portion is substantially free of lower denture plate 12. Base member 16 has a central aperture 17. Central aperture 17 includes female threads that threadably receive a striking pin 18, which is a generally elongated, cylindrical member have male threads along an outer portion of its body which are threadably received in the threaded central aperture 17 of base member 16. Striking pin 18 may include a ball bearing (not shown) rotatably mounted in its free end 19. In order to fix striking pin 18 at a particular threaded height in aperture 17 with respect to base member 17, which could be desirable under certain situations, a small amount of material 38 which may be the same type of material as used in plates 12 and 14 is located in contact with both base member 16 and striking pin 18 such that these elements are fixed in their relative positions.

Figure 10:
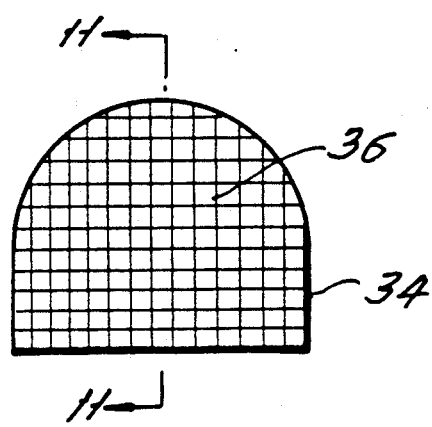
FIG. 10 shows a bottom view of a grid device for indicating when the mandible has been repositioned.
Figure 11:
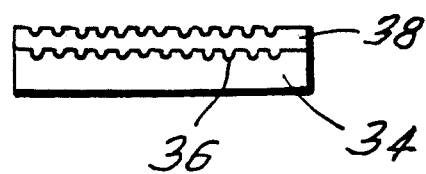
FIG. 11 shows a cross-sectional view of the grid device along lines 11—11 of FIG. 10.

A contact plate 20, as is generally known for recording a Gothic Arch, is mounted upon a lower portion of upper dental plate 14. To provide an indication of when the mandible has been properly repositioned, contact plate 20 is provided with a grid 34 calibrated with markings 36 as shown in the bottom view of the grid 34 shown in FIG. 10. An ink coating 38 (FIG. 11) over the grid 34 is scratched off by the striking pin 18 as lower denture plate 12 is moved due to the person exercising the mandible, as will be discussed below.

The grid is a clear plastic measuring device with vertical and horizontal parallel markings 36 one millimeter apart. It is the exact size and shape as the striking plate. The position of the apex of the Gothic arch on the striking plate is measured by the grid 34 and recorded on the patient's record. When the measurements indicate that no further movement of the apex of the arch has taken place for a period of two weeks, it can be assumed that the desired centric relation has been reached and the dentures can be constructed at this position.

As can be seen in FIG. 4, when training device 10 is positioned in an edentulous individual's mouth (it being understood that only a portion of the gums of such an individual is shown in FIG. 4), base member 16 and contact plate 20 are oriented substantially parallel with respect to each other. Furthermore, for purposes which will become clear below, the trailing edge (shown as the right side edge in FIG. 4) of both base member 16 and contact plate 20 are angled upward with respect to a leading (or left side edge) of the same elements.

Referring now to FIGS. 6-9, the use of training device 10 to posteriorly reposition the mandible will now be described.

FIG. 6 illustrates the profile of a patient who has a protruding mandible. In accordance with the invention, the patient places training device 10 in the mouth for about one hour per day for 10-30 days. The relative positions of the lower plate 12 and upper plate 14 at this point in time are shown in FIG. 8. Over the course of this period, training device 10 acts as a therapeutic, exercising device whereby, when the patient's mouth is closed, the striking pin 18 mounted on lower denture plate 12 contacts contact plate 20 of the upper denture plate 14. This action urges the mandible posteriorly in the direction shown by the arrows in FIG. 6 and 8. The angle of the occlusion is arrived at by trial and error. The angle is set at 7 to 12 degrees off the horizontal. The desired angle is the greatest degree at which the patient can maintain contact of the pin with the plate and produce a Gothic arch tracing. This is determined by a trial fitting with the striking plate set in wax so that it can be adjusted to the optimal angle by trial and error.

After the mandible has been optimally repositioned, which may be determined by visual inspection of the grid located on the indicating means, the relative positions of plates 12 and 14 are as shown (in an exaggerated manner) in FIG. 9, and the position of the individual's mandible is as shown in FIG. 7.

The patient, now with a correctly repositioned mandible, is then fitted for a set of dentures. In accordance with the invention, a particular artificial tooth structure is utilized in order to maintain the repositioned mandible in place. An especially preferred denture tooth structure is disclosed in U.S. Pat. No. 3,252,220, which is herein incorporated by reference.

The structure of two cooperating teeth in accordance with the invention is shown in FIG. 5, and a portion of a row of such teeth as would be found in a posterior portion of a set of dentures is shown in FIG. 5a. Upper artificial tooth 22 is shaped such that a ridge 26 located on one edge of tooth 22 (shown as the right side edge in FIG. 5) contacts a generally concave masticating surface 32 of a lower artificial denture tooth 24. Similarly, ridge 30 located on one edge of tooth 24 (shown as the left side edge in FIG. 5) contacts a generally concave masticating surface 28 located on upper artificial tooth 22. As can be seen in FIG. 5a, the ridges 30 of teeth 24 are arranged in a row at one edge of the masticating surface 32 of each artificial tooth 24. This artificial tooth structure maintains the repositioned mandible in place after training device 10 has been used as shown in FIGS. 6-9 to optimally reposition the same.

Because the angle of occlusion established with the training device is the same used on the teeth themselves, there is no interference by the teeth and the lower jaw will automatically return to its optimal retruded position in function. The restored vertical dimension also prevents the drifting forward due to overclosure.

As will be understood from the foregoing, the training device 10 can be utilized as part of a total system for fitting an edentulous individual with artificial teeth that will be balanced and better fitting for the patient. Specifically, a dentist would, prior to fitting the patient with dentures, reposition the protruding mandible of the patient as discussed above. It has been found that patients fitted with dentures in this manner experience less discomfort due to the dentures poorly fitting the gums.

Although the present invention has been described in connection with a preferred embodiment thereof, many other variations and modifications will now become apparent to those skilled in the art without departing from the scope of the invention. It is preferred therefore, that the present invention not be limited by the specific disclosure herein, but only by the appended claims.

What is claimed is:

1. A method for posteriorly repositioning a protruding mandible of an edentulous individual to an optimal position for the mandible, comprising using a therapeutic, intraoral training device comprising:
   a lower denture plate adapted to fit over the lower gum of the individual, the lower denture plate having:
      a base member fixedly mounted onto an upper portion of the lower denture plate; and
      a striking pin received within the base member, the striking pin being positioned at substantially a right angle to the base member; and
   an upper denture plate adapted to fit over the upper gum of the individual, the upper denture plate having:
      a contact plate fixedly mounted onto a lower portion of the upper denture plate for contact by the striking pin; and
      a grid means for indicating the repositioning movement of the mandible, the grid indicating means being located on the contact plate such that the striking pin contacts the grid indicating means and traces the repositioning movement of the mandible thereon;
   wherein the base member and contact plate are oriented with respect to a horizontal plane such that when the striking pin contacts the contact plate, the device urges the mandible to be posteriorly repositioned to the optimal position, and the posterior movement of the mandible is indicated by the grid indicating means so that optimal repositioning of the mandible can be determined by visual inspection of the grid indicating means, the device being used until the protruding mandible is repositioned to the optimal position.

2. The method of claim 1, wherein the therapeutic, intraoral training device is used for about one hour per day for about 10 to about 30 days.

3. The method of claim 1, wherein the therapeutic, intraoral training device is placed in the oral cavity and the mandible is exercised until the mandible is repositioned to the optimal position.

4. The method of claim 3, wherein the therapeutic, intraoral training device is placed in the oral cavity and the mandible is exercised for about one hour per day for about 10 to about 30 days.

5. A system for fitting an edentulous individual having a protruding mandible with dentures, comprising:
   1) a therapeutic, intraoral training device for posteriorly repositioning a protruding mandible of an edentulous individual to an optimal position for the mandible, said device comprising:
   a lower denture plate adapted to fit over the lower gum of the individual, the lower denture plate having:
      a base member fixedly mounted onto an upper portion of the lower denture plate; and
      a striking pin received within the base member, the striking pin being positioned at substantially a right angle to the base member; and
   an upper denture plate adapted to fit over the upper gum of the individual, the upper denture plate having:
      a contact plate fixedly mounted onto a lower portion of the upper denture plate for contact by the striking pin; and
      a grid means for indicating the repositioning movement of the mandible, the grid indicating means being located on the contact plate such that the striking pin contacts the grid indicating means and traces the repositioning movement of the mandible thereon;

wherein the base member and contact plate are oriented with respect to a horizontal plane such that when the striking pin contacts the contact plate, the device urges the mandible to be posteriorly repositioned to the optimal position, and the posterior movement of the mandible is indicated by the grid indicating means so that optimal repositioning of the mandible can be determined by visual inspection of the grid indicating means; and 2) a set of dentures having posterior teeth having a concave, masticating surface and a ridge located at one edge of the masticating surface for maintaining the posteriorly repositioned mandible in the optimal position.

6. A method for fitting an edentulous individual having a protruding mandible with dentures, comprising the steps of:

1) posteriorly repositioning the protruding mandible to an optimal position using a therapeutic, intraoral training device comprising:

a lower denture plate adapted to fit over the lower gum of the individual, the lower denture plate having:

a base member fixedly mounted onto an upper portion of the lower denture plate; and a striking pin received within the base member, the striking pin being positioned at substantially a right angle to the base member; and an upper denture plate adapted to fit over the upper gum of the individual, the upper denture plate having:

a contact plate fixedly mounted onto a lower portion of the upper denture plate for contact by the striking pin; and a grid means for indicating the repositioning movement of the mandible, the grid indicating means being located on the contact plate such that the striking pin contacts the grid indicating means and traces the repositioning movement of the mandible thereon;

wherein the base member and contact plate are oriented with respect to a horizontal plane such that when the striking pin contacts the contact plate, the device urges the mandible to be posteriorly repositioned to the optimal position, and the posterior movement of the mandible is indicated by the grid indicating means so that optimal repositioning of the mandible can be determined by visual inspection of the grid indicating means, the device being used until the protruding mandible is repositioned to the optimal position; and 2) fitting the individual with a set of dentures having posterior teeth having a concave, masticating surface and a ridge located at one edge of the masticating surface such that the dentures maintain the repositioned mandible in the optimal position.

* * * * *